United States Patent [19]

Selway et al.

[11] Patent Number: 5,070,078

[45] Date of Patent: Dec. 3, 1991

[54] ANTIVIRAL COMPOUNDS

[75] Inventors: John W. T. Selway, Beckenham, England; Lowrie M. Beacham, III, Durham, N.C.; Susan M. Daluge, Chapel Hill, N.C.; Joel Van Tuttle, Durham, N.C.; Thomas A. Krenitsky, Chapel Hill, N.C.

[73] Assignee: Burroughs Wellcome Co., Research Triangle Park, N.C.

[21] Appl. No.: 234,215

[22] Filed: Aug. 19, 1988

[30] Foreign Application Priority Data

Aug. 22, 1987 [GB] United Kingdom ................ 8719877

[51] Int. Cl.$^5$ ........................ A61K 31/00; C07H 19/00
[52] U.S. Cl. ...................................... 514/50; 514/49; 536/23; 424/408
[58] Field of Search ...................... 514/45, 50; 536/23; 424/408

[56] References Cited

U.S. PATENT DOCUMENTS 4,710,492 12/1987 Lin et al. ................................. 536/23
4,880,782 11/1989 Eckstein et al. ....................... 536/23
4,963,662 10/1990 Matthes et al. ........................ 536/27

FOREIGN PATENT DOCUMENTS

| 0254268A3 | 1/1988 | European Pat. Off. . |
| 1913384 | 6/1970 | Fed. Rep. of Germany . |
| 103241 | 1/1974 | Fed. Rep. of Germany . |
| 2026600 | 9/1970 | France . |
| 8800050 | 1/1988 | PCT Int'l Appl. . |
| PCT/EP87/-00719 | 6/1988 | PCT Int'l Appl. . |
| WO90/03978 | 4/1990 | PCT Int'l Appl. .................... 536/23 |
| 1189973 | 4/1970 | United Kingdom . |

OTHER PUBLICATIONS

Ajmera, et al., Article, J. Med. Chem., 1984, 27, 11–14, Synthesis and Biological Activity of 5-Fluoro-2',3'-dideoxy-3fluorouridine and its 5'-Phosphate.

Baba, et al., Antimicrobial Agents and Chemotherapy, Feb. 1987, pp. 337–339, vol. 31, No. 2, Selective Inhibitory Effect of (S)-9-(3-Hydroxy-2-Phosphonylmethoxypropyl)Adenine and 2'-Nor-Cyclic GMP on Adenovirus Replication In Vitro.

Krenitsky, et al., J. Med. Chem., 1983, 26, 891–895, 3'-Amino-2',3'-dideoxyribonucleosides of Some Pyrimidines: Synthesis and Biological Activities.

Beres, et al., J. Med. Chem., 1986, 29, 494–499, Synthesis and Antitumor and Activiral Properties of 5-Alkyl-2'-deoxyuridines, 3',5'-Cyclic Monophosphates, and Neutral Cyclic Triesters.

Matthes, et al., vol. 165, No. 1, 1989, Biochemical and Biophysical Research Communications, pp. 488–495.

Van Aerschot, et al., J. Med. Chem., 1989, 32, pp. 1743–1749, 3'-Fluoro-2',3'-dideoxy-5-chlorouridine: Most Selective Anti-HIV-1 Agent among a series of New 2'-and 3'-Fluorinated 2',3'-Dideoxynucleoside Analogues.

Balzarini, et al., Molecular Pharmacology, 35:571–577, 5-Halogeno-3'-fluoro-2',3'-dideoxyuridines as Inhibitors of Human Immunodeficiency Virus (HIV): Potent and Selective Anti-HIV Activity of 3'-Fluoro-2',-3'-dideoxy-5-chlorouridine.

Balzarini, et al., vol. 158, No. 2, 1989, Biochemical and Biophysical Research Communications, pp. 413–422.

Balzarini, et al., Biochemical Pharmacology, vol. 38, No. 6, 1989, pp. 869–874.

Tetrahedron, vol. 27, 2463–2472 (1971).

Journal F. Prackt. Chemie, 315, 1, 1973, 149–154.

Journal F. Prackt. Chemie, 315, 5, 1973, 895–900.

Acta Biol. Med. Germ., 23, 759–766 (1969).

European Specification 254268.

J. Med. Chem., 1984, 27, 11–14.

J. Med. Chem., 187m 30, 1270–1278.

Cell Biology & Toxicology, vol. 2, No. 4, 1986, 441–445.

J. Med. Chem., 1987, 30, 1270–1278.

Primary Examiner—Johnnie R. Brown
Assistant Examiner—James O. Wilson
Attorney, Agent, or Firm—Donald Brown; Lawrence A. Nielsen; Hannah O. Green

[57] ABSTRACT

2',3'-Dideoxy-3'-fluoro pyrimidine nucleosides particularly 2',3'-dideoxy-3'-fluorothymidine have been found to have particularly potent activity against adenovirus infections especially those caused by adenoviruses of serotype 8. Such compounds are preferably presented in pharmaceutical formulations adapted for ophthalmic administration.

7 Claims, No Drawings

ANTIVIRAL COMPOUNDS

The present invention relates to certain nucleoside derivatives having activity against adenoviruses.

Adenoviruses were first isolated from man in 1953 and at least 41 different serotypes representing 6 subgenera have now been identified. Adenoviruses are responsible, for example, for 5% of acute respiratory infections in children under 4 years of age and are found in 10% of respiratory diseases in this age group requiring hospitalisation. Such conditions are generally associated with pharyngitis, coughing and conjunctivitis. Very often laryngotracheobronchitis occurs which develops into pneumonia in young children, and in fact, 10% of childhood pneumonias are due to adenovirus infection and are often fatal in children under 2 years of age.

In the older population adenoviruses are often responsible for pharyngoconjunctival fever and acute respiratory disease in institutionalised persons where it has been known to have a fatal outcome. The viruses are often associated with pertussis syndrome, haemorrhagic cystitis, meningitis, diarrhoea and epidemic keratoconjunctivitis. The latter condition is characterised by rapid conjunctival involvement with pain, photophobia, lymphadenopathy and subsequent keratitis. The syndrome may last for several weeks but the corneal opacity may endure for several years. The patient is therefore disabled to varying degrees over a period of time. It has been shown that adenovirus type 8 is the major etiologic agent in this particular aspect of adenovirus disease. Adenovirus disease is particularly severe in children with severe combined immunodeficiency disease (SCID) and in immunocompromised hosts. Adenoviruses are recognized also as increasingly more common in patients with Acquired Immune Deficiency Syndrome (AIDS) and in bone marrow transplant recipients. There has hitherto been no useful antiviral compound that is effective in the treatment of adenoviral infections and there is also no adequate vaccine.

We have now discovered that compounds of formula (I) below have potent activity against adenoviruses particularly those of type 8.

The present invention accordingly provides compounds of formula (I)

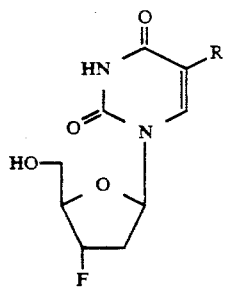

(wherein R represents a hydrogen atom, $C_{1-4}$ alkyl (e.g. methyl), or a halogen atom (e.g. a chlorine, bromine or iodine atom) and physiologically acceptable salts and esters thereof, for use in the treatment or prophylaxis of an adenovirus infection. Such compounds, salts and esters are hereafter referred to as compounds according to the invention.

Particularly preferred compounds of formula (I) by virtue of their especially potent activity against adenoviruses are:

1. 2',3'-dideoxy-3'-fluorothymidine
2. 2',3'-dideoxy-3'-fluorouridine
3. 5-bromo-1-(2,3-dideoxy-3-fluoro-β-D-erythro-pentofuranosyl)uracil
4. 5-iodo-1-(2,3-dideoxy-3-fluoro-β-D-erythro-pentofuranosyl)uracil
5. 5-chloro-1-(2,3-dideoxy-3-fluoro-β-D-erythro-pentofuranosyl)uracil.

Compound No 1 referred to above has particularly high anti-adenovirus activity especially against serotypes 5 and 8.

In a further aspect of the present invention, there is provided the use of a compound according to the invention in the manufacture of a medicament for the treatment of prophylaxis of adenovirus infections.

The present invention further provides a method for the treatment or prophylaxis of an adenovirus infection in a human subject which comprises administering to the said human subject an effective amount of a compound according to the invention.

Examples of adenovirus infections which may be treated or prevented in accordance with the present invention include the clinical conditions referred to above, and particularly adenoviral infections of the eye.

Preferred esters of the compounds of formula (I) include carboxylic acid esters in which the non-carbonyl moiety of the ester grouping is selected from straight or branched chain alkyl, alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); and mono-, di- or tri-phosphate esters. With regard to the above-described esters, unless otherwise specified, any alkyl moieties present in such esters advantageously contain 1 to 18 carbon atoms, particularly 1 to 4 carbon atoms. Any aryl moiety present in such esters advantageously comprises a phenyl group. Any reference to any of the above compounds also includes a reference to a pharmaceutically acceptable salt thereof.

Examples of pharmaceutically acceptable salts of the compound of formula (I) and its pharmaceutically acceptable derivatives include base salts, e.g. derived from an appropriate base, such as alkali metal (e.g. sodium), alkaline earth metal (e.g. magnesium) salts, ammonium and $NX_4^+$ (wherein X is $C_{1-4}$ alkyl).

Certain of the compounds of formula (I) above have been previously described in the literature. For example, the compound of formula (I) above in which R represents a hydrogen atom is described by G. Kowollik et al, Journal f. prakt Chemie, 315(5), 1973, 895–900; and the compound of formula (I) in which R represents a methyl group is described in UK Patent Specification No. 1189973. Also the compound of formula (I) in which R represents a bromine atom is referred to in European Patent Specification No. 254268.

The above compounds of formula (I) in which R represents a chlorine or iodine atom and their physiologically acceptable salts and esters are, however, new compounds and represent further features of the present invention.

The compounds according to the invention may be administered to humans for the prophylaxis or treatment of adenovirus infections and eye infections in particular, by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose will be in the range of 3.0 to 120 mg per kilogram body weight of the patient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of the compound per unit dosage form.

While it is possible for the compounds according to the invention to be administered alone it is preferably to present it as a pharmaceutical formulation. The formulations of the present invention comprise at least one compound according to the invention together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), opthalmic, vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

In view of the activity of the compounds according to the invention against adenovirus infection of the eye, as referred to above, it is particularly preferred to present the compounds according to the invention in the formulations adapted for ophthalmic administration.

Such formulations for ophthalmic administration include eye drops and ophthalmic ointments, creams, suspensions and lotions.

Drops according to the present invention may comprise sterile aqueous or oily solutions or suspensions and may be prepared by dissolving the active ingredient in a suitable aqueous solution of a bactericidal and/or any other suitable preservative. The resulting solution may then be clarified by filtration, transferred to a suitable container which is then sealed and sterilised by autoclaving. Alternatively, the solution may be sterilised by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%).

Lotions according to the present invention include sterile aqueous solutions optionally containing a preservative and may be prepared by methods similar to those for the preparation of drops.

Creams or ointments according to the present invention are semi-solid formulations of the active ingredient particularly for ophthalmic application. They may be made by mixing the active ingredient in finely-divided or powdered form alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage, an oil of natural origin such as almond, corn, arachis, castor or olive oil, wool fat or its derivatives, or a fatty acid such as stearic or oleic acid together with an alcohol such as propylene glycol or macrogols. The formulation may incorporate any suitable surface active agent such as sorbitan esters or polyoxyethylene derivative thereof. Suspending agents such as natural gums, cellulose derivatives or inorganic materials such as silicaceous silicas; and other ingredients such as lanolin may also be included.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus or paste. Oral formulations may further include other agents conventional in the art, such as sweeteners, flavouring agents and thickeners.

A tablet may be made by compression or moulding, optionally with one or more accessory ingredients. Compressed tablets may be prepared by compressing in a suitable machine the active ingredient in a free-flowing form such as a powder or granules, optionally incorporating a binder (e.g. povidone, gelatin, hydroxypropylmethyl cellulose), lubricant, inert diluent, disintegrant (e.g. sodium starch glycollate, cross-linked povidone, cross-linked sodium carboxymethyl cellulose), surface-active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be present as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or daily sub-dose, as herein above recited, or an appropriate fraction, of the compound according to the invention.

The compounds according to the invention may be prepared in conventional manner. Thus, for example, compounds of formula (I) particularly the compound wherein R represents a methyl group may be prepared as described in UK Patent Specification No. 1189973. The compound of formula (I) wherein R represents a hydrogen atom may be prepared as described for example by G. Kowollik et al, J. Prakt. Chem. 1973, 315(5), 895-900.

The compounds of formula (I) in which R represents a halogen (particularly a chlorine, bromine or iodine) atom may be prepared for example by halogenating a corresponding compound of formula (I) in which R represents a hydrogen atom and in which the 5'-hydroxy group is blocked, for example by an acyl group such a p-toluoyl group.

Halogenation of the above starting material may be effected in conventional manner, for example iodination using iodine monochloride, e.g. in methylene dichloride, bromination using bromine e.g. in glacial acetic acid and chlorination using a chlorine complex of iodobenzene, e.g. in glacial acetic acid.

The above toluoyl derivative may be prepared by treating the appropriate compound of formula (I) with the example p-toluoyl chloride, e.g. in pyridine. After halogenation as described above, the p-toluoyl protecting group may be removed for example by sodium methoxide in methanol.

The parent compound of formula (I) may be converted into a physiologically acceptable ester by reaction with an appropriate esterifying agent, e.g. an acid halide or anhydride. The compound of formula (I), including esters thereof, may be converted into pharmaceutically acceptable salt thereof in conventional manner, e.g. by treatment with an appropriate base. An ester or salt may be converted into the parent compound, e.g. by hydrolysis.

The following Examples are intended for illustration only and are not intended to limit the scope of the invention in any way. The term 'active ingredient' as used in the Examples means a compound of formula (I) or a physiologically acceptable salt or ester thereof.

EXAMPLE 1

1-(2,3-Dideoxy-3-fluoro-$\beta$-D-erythro-pentofuranosyl)-5-iodouracil p-Toluoyl chloride (freshly distilled, 352 mg, 2.10 mmol) was added to a solution of 1-(2,3-dideoxy-3-fluoro-$\beta$-D-erythro-pentofuranosyl)uracil (440mg, 1.91 mmol) in dry pyridine (10ml). The solution was stirred at 50° for 1.5 hour, and then at 25° for 18 hours. The pyridine was evaporated and the residue dissolved in CHCl$_3$ (25ml). This solution was extracted with 1M H$_2$SO$_4$ (5ml), then H$_2$O (2×10 ml), and dried (MgSO$_4$). Evaporation of CHCl$_3$ left a colourless glass (0.72g) which was chromatographed on silica gel. Elution with 2% MeOH—CHCl$_3$ gave the 5'-O-toluoyl derivative as white solid foam (0.66g, 90%); chromatography homogeneous on TLC plates (silica gel developed with 5% MeOH—CHCl$_3$); structure confirmed by $^1$H—NMR.

The 5'-O-toluoyl derivative of 1-(2,3-dideoxy-3-fluoro-$\beta$-D-erythro-pentofuranosyl)uracil (200mg, 0.574 mmol), iodine monochloride (139 mg, 0.861 mequiv), and CH$_2$Cl$_2$ (10 ml) were refluxed for 2 hours. The solution was decolourised with a minimum of 2% aqueous NaHSO$_3$ (ca. 2 ml). The aqueous layer was separated and the CH$_2$Cl$_2$ layer washed with H$_2$O (2×5 ml) and dried (MgSO$_4$). Evaporation of CH$_2$Cl$_2$ left a cream colored solid foam (0.25 g) which was dissolved in MeOH (10 ml) and stirred with sodium methoxide (0.57 mmol) under N$_2$ at 25° for 18 hours. The solution was neutralized with Dowex 50W-X8 (H+ form) resin. The resin was filtered off, washed with MeOH, and the contents of the methanol filtrate wash chromatographed on silica gel. Elution with 10% MeOH—CH$_2$Cl$_2$ gave a product as a white solid (0.135 g). Recrystallization from EtOH gave title compound as white crystals (115 mg, 55% overall yield); m.p. 197.5°-198° dec; Anal; Calcd for C$_9$H$_{10}$FN$_2$O$_4$: C, 30.36; H, 2.83; N, 7.87; F, 5.34; I, 35.64. Found: C, 30.50; H, 2.85; N, 7.85; F, 5.31; I, 35.51; UV $\lambda$ max (H$_2$O): 286 nM; structure further confirmed by $^1$H—NMR and mass spectrum.

EXAMPLE 2

5-Bromo-1-(2,3-dideoxy-3-fluoro-$\beta$-D-erythro-pentofuranosyl)uracil

The 5'-O-toluoyl derivative of 1-(2,3-dideoxy-3-fluoro-$\beta$-D-erythro-pentofuranosyl)uracil, prepared as described in Example 1, (200 mg, 0.574 mmol), glacial acetic acid (5 ml) and bromine (0.08 ml of an 8M solution in glacial acetic acid, 0.64 mequiv.) were stirred at 25° for 18 hours. The solution was evaporated to a glass which was treated with sodium methoxide and methanol as described in Example 1. Product was eluted from a silica gel column with 5% MeoH—CH$_2$Cl$_2$ as white crystals (135 mg).

Recrystalization from EtOH gave title compound as white crystals (115 mg, 64% overall yield); m.p. 193.5°-194° dec.; Anal Calcd for C$_9$H$_{10}$BrFN$_2$O$_4$: C, 34.97; H, 3.26; N, 9.06; Br, 25.85; F, 6.15. Found: C, 35.07; H, 3.31; N, 9.00; Br, 25.78; F, 6.04; UV $\lambda$ max (H$_2$O): 277 nM; structure further confirmed by $^1$H—NMR and mass spectrum.

EXAMPLE 3

5-Chloro-1-(2,3-dideoxy-3-fluoro-$\beta$-D-erythro-pentofuranosyl)uracil

The chlorine complex of iodobenzene was freshly prepared as described in the literature (see M. J. Robins, et al., Can. J. Chem. 1982, 60, 554) and 246 mg (0.895 mmol) added to a solution of the 5'-O-toluoyl derivative of 1-(2,3-dideoxy-3-fluoro-$\beta$-D-erythro-pentofuranosyl)uracil (260 mg, 0.746 mmol), prepared as described in Example 1, in glacial acetic acid (4 ml). This solution was maintained at 80° under nitrogen for 20 minutes and evaporated to a white solid foam. Treatment with sodium methoxide in methanol was carried out as in Example 1. Chromatography on 2 mm thick silica gel plates (20×20 cm) developed in CHCl$_3$: MeOH: NH$_4$OH/180:20:1 was required to separate 5-chlorouracil (slightly greater R$_f$) from title compound, isolated as an off-white solid (46 mg). Trituration in methanol gave title compound as white needles (34 mg); m.p. 183°-184°; Anal. Calcd for $C_9H_{10}ClFN_2O_4$: C, 40.85; H, 3.81; Cl, 13.40; N, 10.59. Found: C, 40.71; H, 3.85; Cl, 13.31; N, 10.55; UV λ max ($H_2O$) 275 nM; structure further confirmed by 'H—NMR and mass spectrum.

EXAMPLE 4

Tablet Formulations

The following formulations A, B and C are prepared by wet granulation of the ingredients with a solution of povidone, followed by addition of magnesium stearate and compression.

Formulation A

|   | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 20 |
| (e) Magnesium Stearate | 5 | 3 |
|   | 500 | 300 |

Formulation B

|   | mg/tablet | mg/tablet |
|---|---|---|
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|   | 500 | 300 |

Formulation C

|   | mg/tablet |
|---|---|
| Active Ingredient | 100 |
| Lactose | 200 |
| Starch | 50 |
| Povidone B.P. | 5 |
| Magnesium Stearate | 4 |
|   | 359 |

The following formulations, D and E, are prepared by direct compression of the admixed ingredients. The lactose used in formulation E is of the direct compression type.

Formulation D

|   | mg/capsule |
|---|---|
| Active Ingredient | 250 |
| Pregelatinised Starch NF15 | 150 |
|   | 400 |

Formulation E

|   | mg/capsule |
|---|---|
| Active Ingredient | 250 |
| Lactose B.P. | 150 |
| Avicel | 100 |

|   | mg/capsule |
|---|---|
| Magnesium Stearate | 5 |
|   | 505 |

Formulation F

Controlled Release Formulation

The formulation is prepared by wet granulation of the ingredients (below) with a solution of povidone followed by the addition of magnesium stearate and compression.

|   | mg/tablet |
|---|---|
| (a) Active Ingredient | 500 |
| (b) Hydroxypropylmethylcellulose (Methocel K4M Premium) | 112 |
| (c) Lactose B.P. | 35 |
| (d) Povidone B.P.C. | 28 |
| (e) Magnesium Stearate | 7 |
|   | 700 |

EXAMPLE 5

Capsule Formulations

Formulation A

A capsule formulation is prepared by admixing the ingredients of Formulation D in Example 1 above and filling into a two-part hard gelatin capsule. Formulation B (infra) is prepared in a similar manner.

Formulation B

|   | mg/capsules |
|---|---|
| (a) Active Ingredient | 250 |
| (b) Lactose B.P. | 143 |
| (c) Sodium Starch Glycollate | 25 |
| (d) Magnesium Stearate | 2 |
|   | 420 |

Formulation C

|   | mg/capsule |
|---|---|
| (a) Active Ingredient | 250 |
| (b) Macrogol 4000 BP | 350 |
|   | 600 |

Capsules are prepared by melting the macrogol 4000 BP, dispersing the active ingredient in the melt and filling the melt into a two-part hard gelatin capsule.

Formulation D

|   | mg/capsule |
|---|---|
| Active Ingredient | 250 |
| Lecithin | 100 |
| Arachis Oil | 100 |
|   | 450 |

Capsules are prepared by dispersing the active ingredient in the lecithin and arachis oil and filling the dispersion into soft, elastic gelatin capsules.

Formulation E

Controlled Release Capsule

The following controlled release capsule formulation was prepared by extruding ingredients (a), (b) and (c) using an extruder, followed by spheronisation of the extrudate and drying. The dried pellets were then coated with release-controlling membrane (d) and filled into a two-piece, hard gelatin capsule.

|  | mg/capsule |
| --- | --- |
| (a) Active Ingredient | 250 |
| (b) Microcrystalline Cellulose | 125 |
| (c) Lactose BP | 125 |
| (d) Ethyl Cellulose | 13 |
|  | 513 |

EXAMPLE 6

Injectable Formulation

Formulation A

| Active Ingredient |  | 0.200 g |
| --- | --- | --- |
| Hydrochloric acid solution, 0.1M | q.s. to pH | 4.0 to 7.0 |
| Sodium hydroxide solution, 0.1M | q.s. to pH | 4.0 to 7.0 |
| Sterile water | q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

Formulation B

| Active Ingredient | 0.125 g |
| --- | --- |
| Sterile, pyrogen-free,pH 7 citrate buffer. q.s. to | 25 ml |

EXAMPLE 7

Intramuscular Injection

| Active Ingredient |  | 0.20 g |
| --- | --- | --- |
| Benzyl Alcohol |  | 0.10 g |
| Glycofurol 75 |  | 1.45 g |
| Water for Injection | q.s. to | 3.00 ml |

The active ingredient is dissolved in the glucofurol. The benzyl alcohol is then added and dissolved, and water added to 3 ml. The mixture was then filtered through a sterile micropore filter and sealed in sterile 3 ml amber glass vials (type 1).

EXAMPLE 8

Eye Drops

| Active Ingredient | 0.20 g |
| --- | --- |
| Benzalkonium Chloride | 0.01 g |
| Isotonic, phosphate buffer, pH 7 to | 10.00 ml |

The active ingredient is dissolved in most of the Isotonic phosphate buffer. The benzalkonium chloride is added and dissolved and the batch made to volume with further Isotonic phosphate buffer. The solution is filtered through a sterile, sterilising grade filter and packed into sterile eye drop bottles and sealed.

EXAMPLE 9

Eye Ointment

| Active Ingredient |  | 0.5 g |
| --- | --- | --- |
| Sterile White Soft Paraffin | to | 5.0 g |

The active ingredient is sterilised by dry heat and mixed with the Sterile White Soft Paraffin under aseptic conditions. The resulting dispersion is packed into sterile ophthalmic ointment tubes.

EXAMPLE 10

Ophthalmic Suspension

| Active Ingredient |  | 0.1 g |
| --- | --- | --- |
| Polysorbate 80 |  | 0.005 g |
| Thiomersal |  | 0.001 g |
| Propylene Glycol |  | 0.1 g |
| Water for Injection | to | 5.0 ml |

The Polysorbate 80, Thiomersal and Propylene Glycol are dissolved in most of the Water for Injections. The solution is sterilised by filtration. The sterile, micronised active ingredient is dispersed in the solution under aseptic conditions. The batch is made up to volume with further Water for Injections which has been sterilised previously. The product is packed into sterile eye drop bottles and sealed.

Antiviral Activity

The anti-adenoviral activity of Compound No. 1 referred to above was tested as follows:

Cells of human epithelial cell line NCTC 2544 (EP) were serially passaged from 75 cm$^2$ tissue culture flasks (Corning) at a spilt ratio of 1/20 every 7 days. The growth medium was Eagles BHK medium supplemented with 10% foetal bovine serum and contained 2.5% of 4.4% sodium bicarbonate solution together with 1% of penicillin (5000 IU ml$^{-1}$) and streptomycin (600 μg ml$^{-1}$) (Flow).

A stock of adenovirus of type 8 was prepared in 25 cm$^2$ tissue culture flasks. Flasks were seeded with $2 \times 10^6$ EP cells in growth medium and incubated overnight at 37° C. The medium was decanted and 1.0 ml of stock virus suspension was added to the flask. After 1.0 hr adsorption 10 ml of maintenance medium (as above but with 2% serum) was added to the flask.

The flask were incubated at 37° C. After 72 hrs the classical 'bunch of grapes' cytopathic effect was visible. The flasks were then frozen and thawed 3 times to liberate the virus and stored at $-70°$ C. Viral titres were usually of the order of $4 \times 10^8$ pfu ml$^{-1}$.

The plaque assay was performed in 50 mm diameter plastic tissue culture dishes which were initially seeded with $2 \times 10^6$ EP cells in growth medium and incubated overnight in 5% $CO_2$ at 37° C. Adenovirus was inoculated on to the cell monolayers in 1.0 ml serum-free medium and allowed to adsorb at 37° C. in a $CO_2$ incubator for 1 hr. After adsorption inoculum was removed and 9.0 ml overlay medium was added. This consisted of 0.5% agarose, Eagles BHK medium, 2.5% of 4.4% sodium bicarbonate solution, 1.5% foetal bovine serum, 1% of penicillin/streptomycin solution and 0.5% of 3 M magnesium chloride solution. From day 5 when plaques could be seen in the unstained culture, the cultures were fixed in 10% of 40% formaldehyde solution in phosphate buffered salt solution. After one hour the overlay gel was rinsed from the plate with tap water and the exposed monolayer stained with 2 ml of 0.5% methyl violet in 5% methanol.

EP cells allowed the productive growth of adenovirus and plaques were clearly visible.

The following results was obtained for the activity of the above Compound against adenovirus of serotype 8:

| Compound No. | $IC_{50}(\mu M)$ |
|---|---|
| 1 | 0.005 |

Cytotoxicity Determination

Cytotoxicity was determined by means of the trypan blue exclusion method. NCTC 2544 cells were prepared in growth medium and aliquots added to 25 $cm^3$ tissue culture flasks at approximately $1 \times 10^5$ cells/ml. At 24 hours the flasks were divided and replenished with growth medium. One half of the flasks received growth medium containing 10 fold dilutions of compound thus exposing the cells to 1, 10, and 100 $\mu M$ concentrations. At 24, 48, and 72 hours representative flasks were removed from the incubator and the monolayers washed to remove debris. The cells were resuspended in growth medium and aliquots mixed with an equal volume of trypan blue. Stained and unstained cells were counted in a haemocytometer. Cell counts were adjusted to cells/ml. An estimate of the growth and viability of treated and untreated cells was then made.

The 50% cell culture inhibitory concentration of compound No. 1) was 38 $\mu M$ at 72 hours.

Preparation of 1-(2-Deoxy-5-(p-chlorobenzoyl)-β-D-threo-pentofuranosyl)-thymine 1-(2-Deoxy-β-D-threo-pentofuranosyl)thymine (J. J. Fox and N. C. Miller J. Org. Chem., 1963, 28, 936) (49.0 g) was dissolved in 500 ml of anhydrous pyridine in a 1L round bottom flask equipped with an addition funnel, nitrogen inlet and mechanical stirrer. The solution was cooled to 5° C. in an ice bath and 4-chlorobenzoyl chloride (35.4 g, 0.202 mol) was added dropwise over 30 minutes. The solution was allowed to gradually warm to ambient temperature. The reaction was quenched with water (20 ml), most of the pyridine removed by rotary evaporation and the residual oil dissolved in ethyl acetate (1 L). The organic solution was washed with 700 ml portions of water, 1,2N HCl and 10% aqueous sodium bicarbonate and dried over sodium sulphate. The mixture was then filtered and solvent removed by rotary evaporation affording 1-(2-deoxy-5-(p-chlorobenzoyl)-D-threo-pentofuranosyl)thymine (62.1 g,80.7%) as an off-white solid suitable for use in the next step: 1H NMR (DMSO-d6) 1.76 (d, J=0.9 Hz, 3H, C-5 $CH_2$), 2.1–2.6 (m, 2H, C-2'), 3.8–4.5 (m, 4H, C-3'H, C-4'H and C-5'H), 5.55 (d, J=2.6 Hz, 1H, C-3'OH), 6.13 (doublet of doublets, J=2.8Hz and 8.3Hz, 1H, C-1'H), 7.58 (d, J=8.6 Hz, 2H, ArH), 7.81 (m, 1H, C-6H), 7.85 (d, J=8.6 Hz, 2H, ArH); TLC, Rf=0.72, silica gel, $CHCl_3:CH_3OH/90:10$.

Preparation of 3'-Deoxy-3'-fluoro-thymidine

A suspension of 1-(2-deoxy-5-(p-chlorobenzoyl)-β-D-threo-pentofuranosyl)-thymine (61.0 g) and potassium carbonate (30.0 g) in methylene chloride (700 ml) was cooled to −78° C. in a 2 L round bottom flask equipped with a mechanical stirrer, addition funnel and nitrogen inlet. Diethylamino sulfurtrifluoride (30 ml) was added dropwise over 10 minutes and stirring was continued an additional 2.5h at −78° C. The solution was warmed to room temperature, transferred to a separatory funnel and washed with ice water (700 ml), and 500 ml portions of water, 1.2N hydrochloric acid and 10% aqueous sodium bicarbonate. The solvent was removed by rotary evaporation and the residue was dissolved in methanol (500 ml). Solid sodium bicarbonate (15 g) was added and the suspension was heated 2h at reflux. The mixture was cooled to room temperature, filtered, solvent removed by rotary evaporation and the residual oil purified by flash chromatography using a 3×36 inch volume of flash silica gel. The column was eluted with 96:4/$CHCl_3:CH_3OH$ while collecting 200 ml fractions. Fractions 29–41 were concentrated by rotary evaporation, the residue slurried in acetone (100 ml) and the solids collected by filtration affording 7.70 g (19.9%) of 3'-deoxy-3'-fluorothymidine: mp=169°–171° C.; TLC, Rf=0.53, Silica Gel, 90:10/$CHCl_3:CH_3OH$; Elemental Analysis: Calc C, 49.18; H, 5.37; N, 11.47; Found C, 49.00; H 5.38; N, 11.40.

We claim:

1. A formulation in a form for ophthalmic administration comprising the compound 5-chloro-1-(2,3-dideoxy-3-fluoro-β-D-erythro-pentofuranosyl) uracil and a pharmaceutically acceptable carrier therefor.

2. A compound of formula (I)

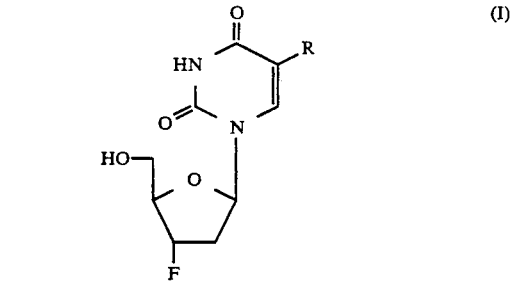

wherein R represents a chlorine atom, or a physiologically acceptable salt thereof.

3. 5-chloro-1-(2,3-dideoxy-3-fluoro-β-D-erythro-pentofuranosyl) uracil.

4. A physiologically acceptable salt of 5-chloro-1-(2,3-dideoxy-3-fluoro-β-D-erythro-pentofuranosyl) uracil.

5. A pharmaceutical composition comprising the compound 5-chloro-1-(2,3-dideoxy-3-fluoro-β-D-erythro-pentofuranosyl) uracil and a pharmaceutically acceptable acceptable carrier therefore.

6. The composition of claim 5, in the form of a tablet or capsule.

7. A pharmaceutical composition comprising 5-chloro-1-(2,3-dideoxy-3-fluoro-β-D-erythro-pentofuranosyl) uracil or a physiologically acceptable salt thereof and a pharmaceutically acceptable carrier therefor.

* * * * *